United States Patent [19]
Harris et al.

[11] Patent Number: 6,060,646
[45] Date of Patent: May 9, 2000

[54] TOLERANCE OF TRICHOTHECENE MYCOTOXINS IN PLANTS AND ANIMALS THROUGH THE MODIFICATION OF THE PEPTIDYL TRANSFERASE GENE

[75] Inventors: Linda Harris, Greely; Steve Gleddie, Ottawa, both of Canada

[73] Assignees: Her Majesty the Queen in right of Canada, as represented by the Minister of Agriculture; Agri-Food Canada, both of Canada

[21] Appl. No.: 08/909,828

[22] Filed: Aug. 12, 1997

[51] Int. Cl.$^7$ ................................ A01H 1/00; A01H 5/00; C07H 21/04; C12N 15/00
[52] U.S. Cl. ...................... 800/301; 800/279; 435/320.1; 435/420; 536/23.2
[58] Field of Search ................................... 800/301, 279; 435/320.1, 420; 536/23.2

[56] References Cited

U.S. PATENT DOCUMENTS

| 4,816,406 | 3/1989 | Desjardins | 435/254 |
| 5,498,431 | 3/1996 | Lindner | 426/238 |

FOREIGN PATENT DOCUMENTS

| 4108746 | 3/1991 | Germany . |
| 9413790 | 6/1994 | WIPO . |
| 9507989 | 3/1995 | WIPO . |
| 9606175 | 2/1996 | WIPO . |
| 9620595 | 7/1996 | WIPO . |

OTHER PUBLICATIONS

Biological Abstracts vol. 72, No. 2691, Picard–Bennon, M. et al., "Search for ribosomal mutants in Podospora–anserina genetic analysis of cold sensitive mutants" (1980).
Kim, Y. et al. (1990). "Two evolutionarily divergent genes encode a cytoplasmic ribosomal protein of *Arabidopsis thaliana*", Gene 93:177–182.
Schindler, D. et al. (1974). "Trichodermin resistance–mutation affecting eukaryotic ribosomes," Nature 248:535–536.
de la Fuente–Martinez, J.M. et al. (1996). "Expression of a bacterial phaseolotoxin resistant ornithyl transcarbamylase in transgenic tobacco confers resistance to *Pseudomonas syringae* pv. *phaseolicola*," Biotechnology 10:905–909.
Dissertation Abstracts No. 91:4157, Kim, Y. et al., "Ribosomal protein gene expression and trichothecene resistance in *Arabidopsis thaliana*," Dissertation, Ohio State University (1991).
Dissertation Abstracts No. 96:8168, Zeisler, J., "Analysis of Gene Clones Thought to Code for *Saccharomyces cerevisiae* Ribosomal Proteins and Construction of a Plasmid Vector Suitable for Gene Cloning in Yeast." (1996).
Dissertation Abstracts No. 97:71410, Trapp, S.C., "Isolation and Characterization of Macrocyclic Trichothecene Biosynthetic Pathway Genes from . . . Sporotrichiodes." (1997).
Posselt, U.K. et al. (1994).j "Improvement of snow mould resistance by conventional and in vitro techniques," Euphytica, 77:251–255.
Miedaner, T. et al. (1997). "Breeding wheat and rye for resistance to Fusarium diseases," Plant Breeding 116:201–220.
Lemmens, M., et al. (1994). "Breeding for head blight (Fusarium spp.) resistance in wheat: development of mycotoxin–based selection method of seedlings," ACTA Horticulturae, 355:223–232.
Bruins, M.B.M. et al. (1993). "Phytotoxicity of deoxynivalenol to wheat tissue with regard to in vitro selection for fusarium head blight resistance," Plant Science 94:195–206.
Nishi, R. et al. (1993). "The primary structure of two proteins from the large ribosomal subunit of rice." *Biochim. et Biophys. Acta* 1216:110–112.
Shultz, L.D. and Friesen, J.D. (1983). "Nucleotide sequence of the tcm1 gene (ribosomal protein Ls) of *Saccharmyces cerevisiae.*" *J. Bact.* 155:8–14.
Fried, H.M. and Warner, J.R. (1981). "Cloning of yeast gene for trichodermin resistance and reibosomal protein L3." *Proc. Natl. Acad. Sci. USA* 78:238–242.
Grant, P.G. et al. (1976). "Mapping of trichodermin resistance in *Saccharomyces cerevisiae*: A genetic locus for a component of the 60S ribsomal subunit." *Genetics* 83:667–673.

*Primary Examiner*—Bruce R. Campell
*Attorney, Agent, or Firm*—Rothwell, Figg, Ernst & Kurz, P.C.

[57] ABSTRACT

*Fusarium graminearum* is a plant pathogen, attacking a wide range of plant species including corn (ear and stalk rot), barley, and wheat (head blight). Fusarium epidemics result in millions of dollars of loses in crop revenues. *Fusarium graminearum* infection in the cereals reduces both grain yield and quality. Mycotoxins are produced by many fungal Fusarium species and thus the grain becomes contaminated with these mycotoxins, such as the trichothecenes. The major trichothecene produced by *F. graminearum* is deoxynivalenol (abbreviated as DON, also known as vomitoxin). Trichothecenes are potent protein synthesis inhibitors and are quite toxic to humans and livestock. A yeast gene has been identified which is resistant to the trichothecene, trichodermin. A corresponding plant gene has been prepared, which has been used to transform plants and would be suitable to transform animals. These transformed plants have an increased resistance to Fusarium infestation. Potentially, transformed animals could have an increased tolerance to the trichothecene mycotoxins.

18 Claims, 6 Drawing Sheets

```
SCRPL13PWT -  M S H R K Y E A P R H G H L G F L P R K R A A S I R A R V K A F P K D D R S K P V A L T S F L G Y K
SCRP13PRO  -  M S H R K Y E A P R H G H L G F L P R K R A A S I R A R V K A F P K D D R S K P V A L T S F L G Y K

SCRPL13PWT -  A G M T T I V R D L D R P G S K F H K R E V V E A V T V V D T P P V V V G V V G Y V E T P R G L R
SCRP13PRO  -  A G M T T I V R D L D R P G S K F H K R E V V E A V T V V D T P P V V V G V V G Y V E T P R G L R

SCRPL13PWT -  S L T T V W A E H L S D E V K R R F Y K N W Y K S K K K A F T K Y S A K Y A Q D G A G I E R E L A R
SCRP13PRO  -  S L T T V W A E H L S D E V K R R F Y K N W Y K S K K K A F T K Y S A K Y A Q D G A G I E R E L A R

SCRPL13PWT -  I K K Y A S V V R V L V H T Q I R K T P L A Q K K A H L A E I Q L N G G S I S E K V D W A R E H F E
SCRP13PRO  -  I K K Y A S V V R V L V H T Q I R K T P L A Q K K A H L A E I Q L N G G S I S E K V D W A R E H F E

SCRPL13PWT -  K T V A V D S V F E Q N E M I D A I A V T K G H G F E G V T H R W G T K K L P R K T H R G L R K V A
SCRP13PRO  -  K T V A V D S V F E Q N E M I D A I A V T K G H G F E G V T H R W G T K K L P R K T H R G L R K V A

SCRPL13PWT -  C I G A W H P A H V M W S V A R A G Q R G Y H S R T S I N H K I Y R V G K G D D E A N G A T S F D R
SCRP13PRO  -  C I G A [C] H P A H V M W S V A R A G Q R G Y H S R T S I N H K I Y R V G K G D D E A N G A T S F D R

SCRPL13PWT -  T K K T I T P M G G F V H Y G E I K N D F I M V K G C I P G N R K R I V T L R K S L Y T N T S R K A
SCRP13PRO  -  T K K T I T P M G G F V H Y G E I K N D F I M V K G C I P G N R K R I V T L R K S L Y T N T S R K A
```

TOLERANCE OF TRICHOTHECENE MYCOTOXINS IN PLANTS AND ANIMALS THROUGH THE MODIFICATION OF THE PEPTIDYL TRANSFERASE GENE

The present invention relates to a modified gene, wherein a host transformed with said gene is resistant to trichothecene mycotoxins, wherein the wild type form of said gene encodes a peptidyl transferase. The present invention also relates to a method of using said gene to transform plants to provide increased resistance against trichothecene mycotoxins. The present invention also relates to a method of using said gene to transform animals to increase the animal's tolerance to the trichothecene mycotoxins. The present invention further relates to a method of using the gene as a selectable marker in transformation.

BACKGROUND OF THE INVENTION

Globally, *Fusarium graminearum* is an important plant pathogen, attacking a wide range of plant species including many important crop plants such as corn (ear and stalk rot), barley, and wheat (head blight). Favourable environmental conditions (conducive temperatures and high humidity) can result in Fusarium epidemics and millions of dollars lost in crop revenues. *Fusarium graminearum* infection in the cereals reduces both the yield and quality of the grain. The reduction of quality is a result of the mycotoxins produced by this species of fungus; these fungal toxins remain in the contaminated cereal after harvest and pose serious health risks to animals and humans who may consume the grain.

Low levels of contamination in non-epidemic years still account for 5% grain losses to Ontario corn farmers, a figure which translates into approximately $27 Million to the swine industry which uses this corn for feed. In epidemic years, this dollar figure can double or triple. These direct losses to growers include the crop and animal losses associated with reduced feed and poorer quality feed. Overall, the FOA of the United Nations estimates that 25% of the world's food crops are affected by mycotoxins each year (Mannon and Johnson, 1985, Fungi down on the Farm, New Scientist 105: 12–16). Fusarium mycotoxins are found in all the major cereal species including corn, wheat, barley, oats, rye and others. The disease is most prevalent in temperate climates.

Mycotoxins, or fungal toxins, are produced by many species of fungi. The species *Fusarium graminearum* is capable of producing a class of compounds known as the trichothecenes. This large family of sesquiterpene epoxides are closely related and vary by the position and number of hydroxylations and substitutions of a basic chemical structure. The major trichothecene produced by *Fusarium graminearum* is deoxynivalenol (DON) also known as vomitoxin for its ability to induce vomiting. These chemicals are potent eukaryotic protein synthesis inhibitors, toxic to both humans and animals, and other organisms such as plants.

Due to their toxicity, safety threshold values have been recommended for DON mycotoxin contamination in grain used for human and animal feed. These values are currently established at 2 ppm of DON in non-staple food stuffs for human consumption, 0.1 ppm in breadwheat and staple foodstuffs, and 1 ppm in infant foodproducts. For livestock feed, the recommended levels are 1 ppm of the complete diet for swine and lactating cattle and 5 ppm for poultry and non-lactating cattle (Underhill, CFIA Fact Sheet, Mycotoxins, 1996). The danger to livestock producers is that if livestock animals are fed contaminated grain they suffer severe health hazards, which include reduction of feed intake, reduced growth rate, reduced fertility, immunosuppression, diarrhea, vomiting and possible death. Some of these effects are directly observable and therefore measurable, such as weight loss, whereas other effects, such as immunosuppression, are more subtle and less quantifiable. In general, a reduction of 10 to 20% of the farrowing rate of swine combined with a 10 to 20% reduction in animal growth rates can cause an approximate 17 to 44% reduction in profit margin for hog producers. The effects of mycotoxins on poultry and cattle are less quantified since both of these species are less sensitive to DON contamination in their feed, and detailed economic threshold assessments have not been made.

During years of Fusarium epidemics, grain which is above the safety threshold of 2 ppm DON for human consumption must be downgraded to animal feed. If the grain contains more than 10 ppm DON, it is rendered unfit for animal feed and must be disposed of. Since many farmers use their own cereals for on-farm animal feed, and they may not be capable of assessing the level of mycotoxin contamination of the grain, a considerable amount of DON-contaminated feed is used. Thus it is important to minimize the level of trichothecenes in food stuffs, which can be accomplished by controlling the outbreaks of Fusarium species in cultivated cereal species.

Chemical treatment has been used in the past to control trichothecene biosynthesis. One such inhibitor is ancymidol, which has been described in U.S. Pat. No. 4,816,406. However, in the present environment, it is desirable to avoid chemical control, especially in food stuffs. Thus, there is a need for a method of controlling the outbreaks of Fusarium species, particularly *F. graminearum* by using non-chemical methods.

Trichothecenes have been shown to act as virulence factors in wheat head scab. This was demonstrated by inoculating wheat heads with trichothecene-nonproducing mutants of *F. graminearum* in which the first gene specific to the trichothecene biosynthetic pathway had been disrupted through genetic engineering (Desjardins et al., 1996, Mol. Plant-Micr. Int. 9:775–781). In two years of field trials, the trichothecene-nonproducing strains were less virulent than the trichothecene-producing progenitor or revertant strains, as measured by several disease parameters. Similar results have been obtained from the inoculation of field-grown corn with these trichothecene-producing and -nonproducing Fusarium strains. Therefore, increasing the tolerance of wheat or corn to the effects of trichothecenes should lead to reduced disease.

SUMMARY OF THE INVENTION

Animal studies have concluded that the biological response to trichothecene mycotoxins is rapid whether the route of administration is oral, topical or parenteral. Prior to their excretion from the body which usually occurs within 24 to 72 hrs after injection, the highest concentration of toxin is usually found in the bile, gallbladder, kidneys, liver and intestines.

The mode of action of all trichothecenes is related to their ability to bind the 60S ribosomal subunit and essentially inhibit peptidyl transferase activity. This is either accomplished by inhibiting the initiation of protein synthesis, the elongation of the growing peptide chain or termination of the peptide (Freinberg and McLaughlin, 1989, Biochemical mechanism of action of trichothecene mycotoxins In: Trichothocene Mycotoxicosis: Pathophysiologic Effects Vol 1

CRC Press, Boca Raton Fla.). The effect of these toxins on protein synthesis is observed in a diverse array of eukaryotic cells such as yeast and mammalian cell lines. Each ribosome has apparently only one binding site for the toxin, and much data suggests that all of the trichothecenes compete for the same ribosomal binding site, peptidyl transferase.

The *Saccharomyces cerevisiae* (yeast) mutant which was spontaneously isolated by Schindler et al. (1974, Nature, 249: 38–41) was shown to be capable of growth on the trichothecene drug trichodermin. This yeast line was demonstrated to have altered 60S ribosomal subunit function and when the gene responsible was cloned, it was found to code for a ribosomal protein L3, or peptidyl transferase (Schultz and Friesen, 1983, J. Bacteriol. 155:8–14).

In one aspect of the present invention, information obtained by comparing the wild type yeast gene and the mutant yeast gene was used to modify the corresponding gene from rice *Oryza sativa,* a cereal plant species. Transgenic tobacco plants were then created, using the modified rice gene, and these plants demonstrated a higher tolerance to the trichothecene mycotoxins than wild type tobacco plants, or plants transformed with the wild-type rice gene. Thus this modified rice gene can provide protection against trichothecene mycotoxins and therefore provide resistance to Fusarium infestation in another plant species.

Thus according to the present invention there is provided a modified gene, wherein a host transformed with said gene has an increased resistance to trichothecene mycotoxins, wherein the wild type form of said gene encodes a peptidyl transferase.

In one embodiment of this aspect of the invention the gene encoding the peptidyl transferase is from rice.

The present invention further provides a suitable cloning vector containing said modified peptidyl transferase gene.

In a further aspect of the invention there is provided a transformed plant, transformed with the modified peptidyl transferase gene, wherein said transformed plant has increased resistance to Fusarium infestation.

The present invention also includes the seed from the transformed plant, referred to above.

In yet a further aspect of the invention there is provided a transformed animal, transformed with the modified peptidyl transferase gene, wherein said transformed animal has an increased tolerance to trichothecene mycotoxins.

In yet another aspect of the present invention there is provided a method of increasing resistance to Fusarium infestation by transforming a suitable plant with a modified gene, wherein the plant transformed with said gene has increased resistance to trichothecene mycotoxins, and wherein the wild type form of said gene encodes a peptidyl transferase.

The present invention also provides a method of increasing tolerance to trichothecene mycotoxins by transforming a suitable animal with a modified gene, wherein the animal transformed with said gene has increased tolerance to trichothecene mycotoxins, and wherein the wild type form of said gene encodes a peptidyl transferase.

In a further aspect of the present invention there is provided a method of using the modified gene of the invention as a selectable marker in transformation experiments.

BRIEF DESCRIPTION OF THE DRAWINGS

These and other features of the invention will become more apparent from the following description in which reference is made to the appended drawings wherein: FIG. 1 shows a comparison of the wild-type Rpl3 amino acid sequence (RPL13PWT; SEQ ID No.: 1) and the Trichodermin-resistant yeast sequence (SCRP 13 PRO; SEQ ID No.: 2). The amino acid change W-255 to C-255 is shown.

Figure 2:
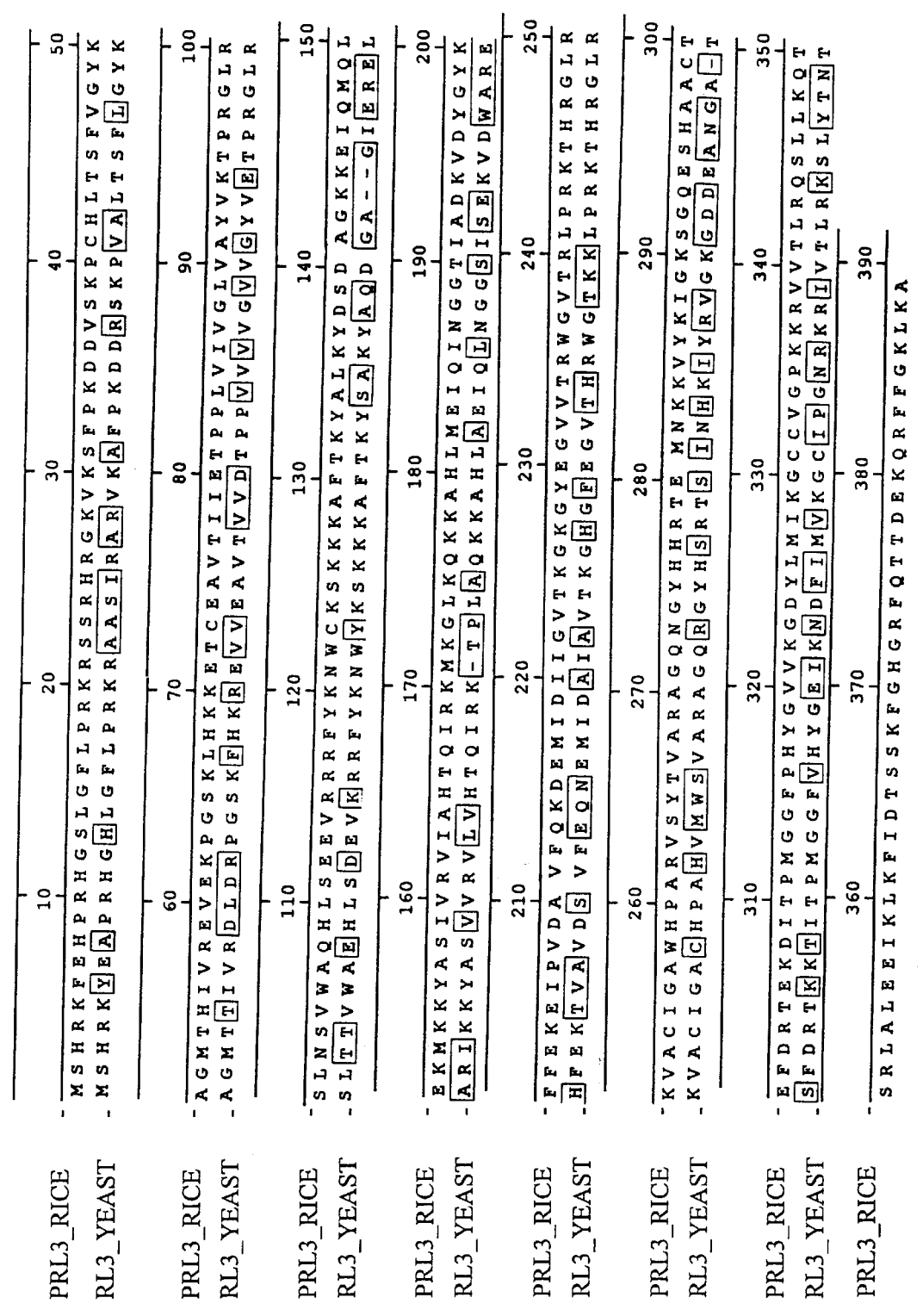

FIG. 2 shows the comparison of the rice Rpl3 sequence (SEQ ID No.: 3) and the trichodermin-resistant yeast sequence (SEQ ID No.: 2). This comparison led to the predicted change of residue W258 (rice numbering) to C258, to create the mycotoxin tolerant rice gene Rpl3:c258.

FIG. 5A), or the modified version of RPl3 (C4 cells; FIG. 5B). Cells were grown in medium containing either no toxin or 25 ppm DON.

DETAILED DESCRIPTION OF INVENTION

Figure 3:
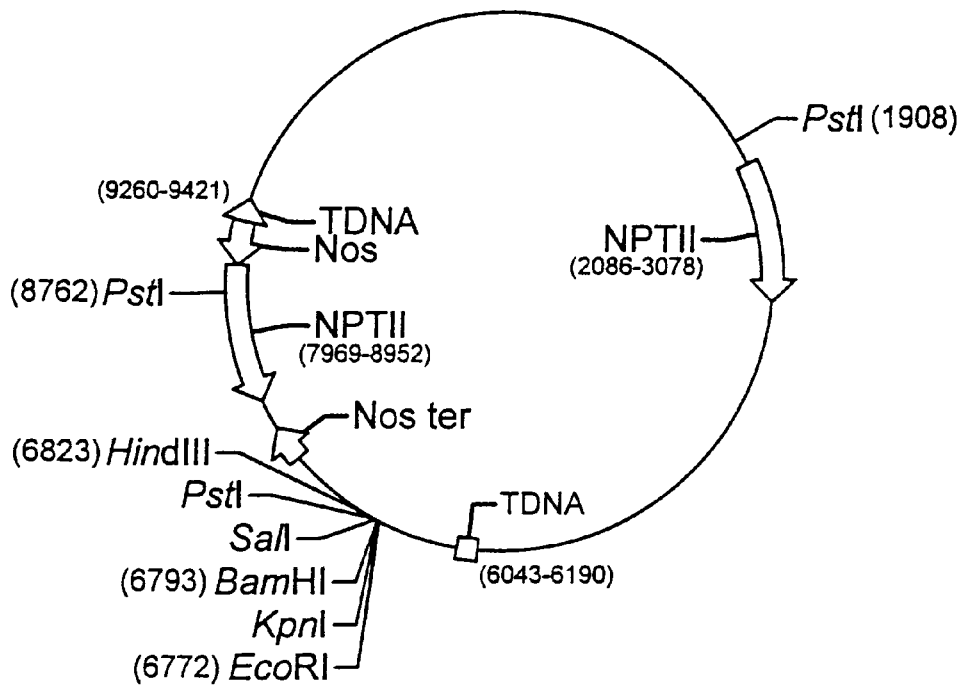
FIG. 3 shows the plasmid map of the *Agrobacterium tumefaciens* binary vector pbin 19 for plant transformation (Bevan, M. 1984, Nucleic Acids Research 12:8711–8721).
Figure 4:
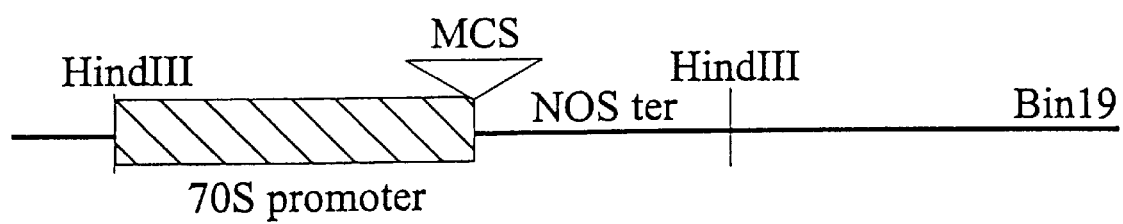
FIG. 4 shows the plasmid pCAMterX, which was used to clone the Rpl3 genes 30 into the multiple cloning site (MCS). The Rpl3 genes were expressed under the direction of the Cauliflower mosaic virus (CAMV 35S promoter) arranged in tandem. (70S promoter).
Figure 5A:
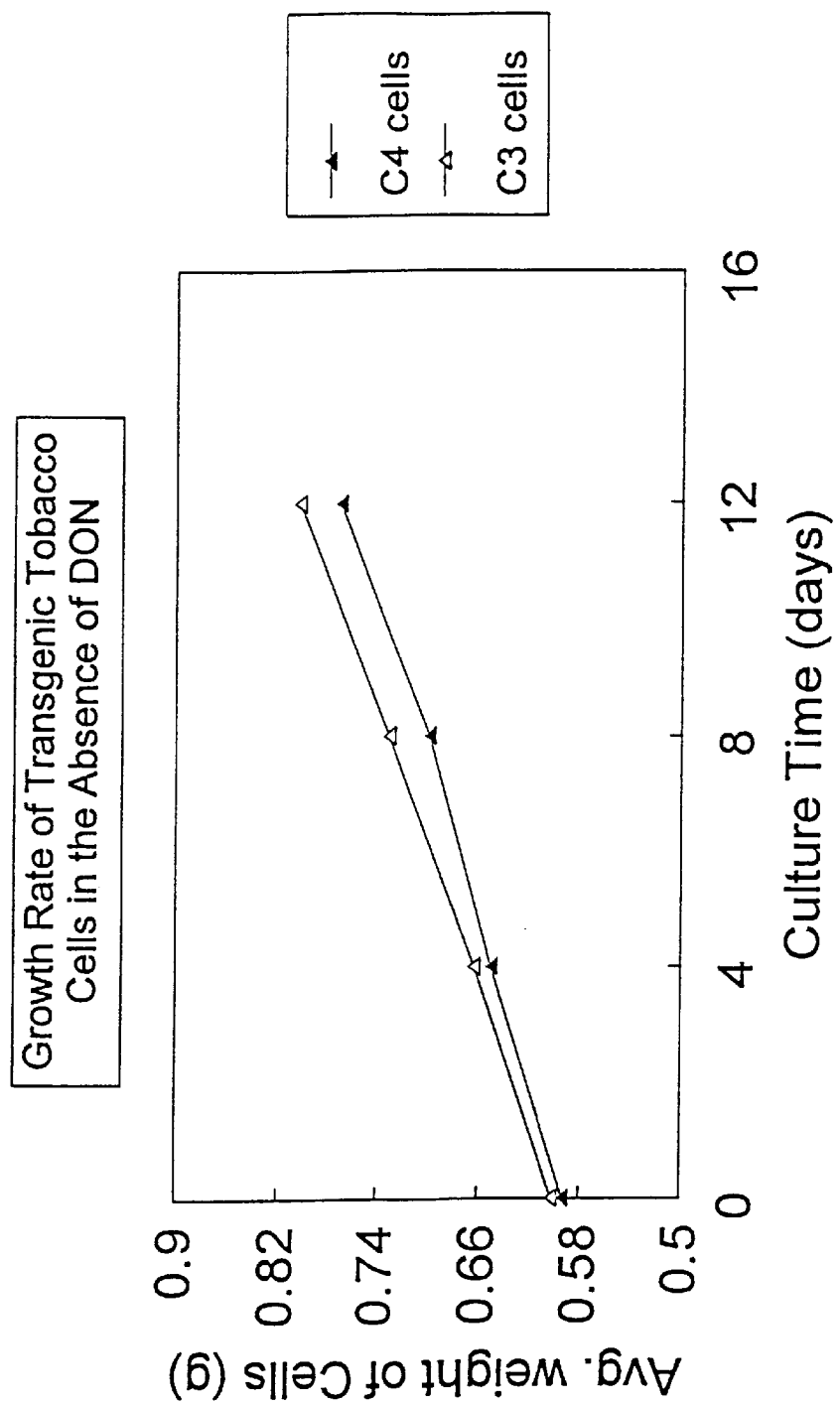
FIGS. 5A–5B show the growth rate of transgenic tobacco cells containing either the wild-type rice Rpl3 gene (C3 cells.
Figure 5B:
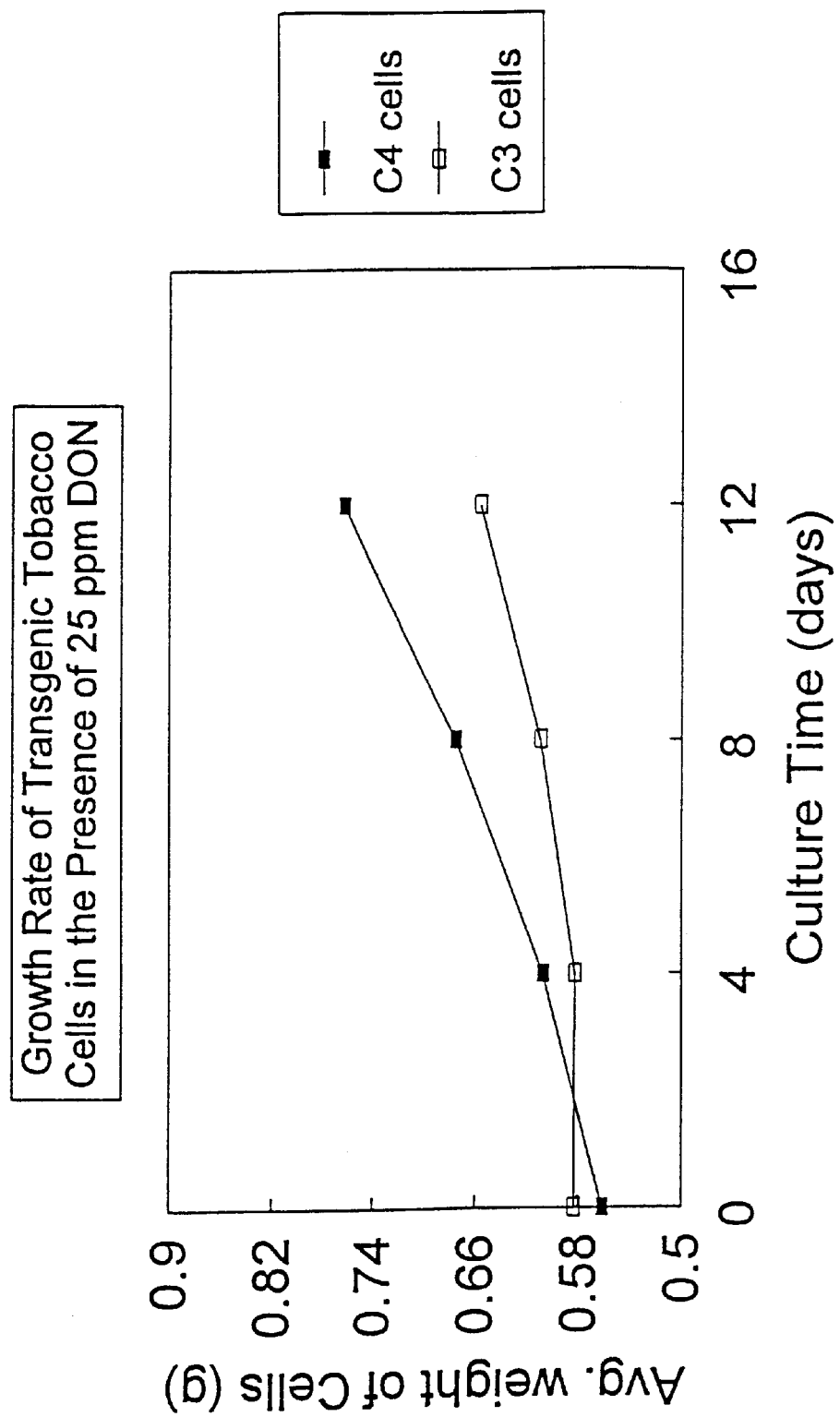

According to the present invention there is provided a modified peptidyl transferase gene, whose gene product provides resistance to trichothecene mycotoxins. Previous work has shown that the trichothecenes bind to a single site on the eukaryotic 60S ribosome. A spontaneous mutant from the yeast *S. cerevisiae,* which is resistant to the trichothecene drug, trichodermin, has been identified. The corresponding wild type gene was identified and the nature of the mutant gene was found to result from a single amino acid change at position 255 of the proposed RPL3 protein.

This mutant represents only one example of a number of possible mutants of the same gene which would result in resistant to the drug trichothecene trichodermin. Thus, the present invention is directed to a modified peptidyl transferase gene, wherein said modified gene provides resistance to the trichothecenes.

Not wanting to be bound by any particular theory, it is believed that the mycotoxin binds to the wild type protein but not to the mutant gene product. Thus the modified peptidyl transferase gene of the present invention would still have to function in the ribosomal complex as a peptidyl transferase, but it would be modified to a sufficient extent to reduce the mycotoxin binding capabilities. If the mycotoxin has a reduced effect the plant can defend itself against the fungus and thus reduce the incidence of disease.

In one embodiment of this aspect of the invention the gene encoding the peptidyl transferase is from a plant. In one example of this embodiment, the corresponding rice Rpl3 gene was identified and modified to reflect the modification in the yeast mutant gene. The resulting Rpl3 gene also showed resistance to the trichothecenes. A plant source of the peptidyl transferase gene was chosen in place of the yeast gene, as it was anticipated that the plant gene would have an improved expression in a plant host, than would the yeast gene. Rice was chosen because it is most closely related to wheat and corn, two examples of plant hosts.

Although the rice peptidyl transferase gene was used as an example other suitable plant genes could also have been used. Suitable examples include: the corresponding gene from *Arabidopsis thaliana* and monocotyledonous sources, for example wheat and corn. For animal transformation the corresponding bovine gene would be a suitable target for modification.

As noted previously, the invention is not limited to the use of modified plant peptidyl transferase genes to confer resistance to the trichothecenes. Any suitable modified animal or plant peptidyl transferase gene that confers resistance to the trichothecenes can be used according the present invention to transform plants or animals to provide trichothecene resistance.

The area of modification in the yeast gene is in a highly conserved area. Shown below in Table 1 is the amino acid homology which occurs around this critical part of the protein, in plants, rats, mice, humans, yeast, *C. elegans* and *Escherichia coli*. Any of these could be used as source material for the peptidyl transferase gene. In each case the amino acid sequence would be aligned with the mutant yeast gene and the corresponding mutation made in the corresponding peptidyl transferase gene. As the entire area between the amino acid residue 240 and 263, based on the amino acid numbering is yeast, is highly conserved, it is considered part of the present invention to modify any of the amino acids within this region to obtain a modified gene sequence. The modification could include substitutions or short length deletions, additions or inversions. As noted previously the modified gene product must continue to function as a peptidyl transferase, but have reduced binding capabilities to the mycotoxin.

signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the modified peptidyl transferase gene of the present construct can be used for expression in plants, without any additional region.

The vectors of the present invention can also contain a suitable promoter. In the plant transformation examples of the present invention any strong promoter will be suitable. Suitable examples include but are not limited to the Cauliflower mosaic virus (CAMV 35S). It can be used alone or together with other plant promoters.

The cloning vector of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene.

TABLE 1

Comparison of the Sequence of Various Peptidyl Transferase Enzymes Between Residues 240 and 263
Amino Acid Sequence

|  | Residue 240 |  |  |  |  |  |  |  |  |  |  |  |  |  |  |  |  | 258 |  |  |  |  |  | 263 |
|---|---|---|---|---|---|---|---|---|---|---|---|---|---|---|---|---|---|---|---|---|---|---|---|---|
| Rice | R |  |  |  |  |  |  |  |  |  |  |  |  |  |  |  |  |  |  |  |  |  |  | R |
| Arabidopsis 1 | R |  |  |  |  |  |  |  |  |  |  |  |  |  |  |  |  |  |  |  |  |  |  | R |
| Arabidopsis 2 | R |  |  |  |  |  |  |  |  |  |  |  |  |  |  |  |  |  |  |  |  |  |  | R |
| YEAST(wt) | K | L | P | R | K | T | H | R | G | L | R | K | V | A | C | I | G | A | W | H | P | A | H | V |
| Bovine |  |  |  |  |  |  |  |  |  |  |  |  |  |  |  |  |  |  |  |  |  |  |  | R |
| Rat |  |  |  |  |  |  |  |  |  |  |  |  |  |  |  |  |  |  |  |  |  |  |  | R |
| Mouse |  |  |  |  |  |  |  |  |  |  |  |  |  |  |  |  |  |  |  |  |  |  |  | R |
| Human 1 |  |  |  |  |  |  |  |  |  |  |  |  |  |  |  |  |  |  |  |  |  |  |  | R |
| Human 2 |  |  |  |  |  |  |  |  |  |  |  |  |  |  |  |  |  |  |  |  |  |  |  | R |
| Human 3 |  |  |  |  |  |  |  |  |  |  |  |  |  |  |  |  |  |  |  |  |  |  |  | R |

Bars represent amino acids identical to the wildtype yeast Rpl3 sequence.

The present invention further provides a suitable cloning vector containing said modified peptidyl transferase gene. Any cloning vector can be used. The cloning vector chosen will of course reflect the host in which the final transformation will be made. The present invention includes both transformed animals and plants.

Suitable plant cloning vectors can include: the binary Agrobacterium vectors, such as Bin 19 (Bevan, M., 1984, Nucleic Acids Research 12:8711–8721) and the vectors used for microprojectile bombardment of monocots.

For the transformation of plants the cloning vector can further comprise a 3' untranslated region. A 3' untranslated region refers to that portion of a gene comprising a DNA segment that contains a polyadenylation signal and any other regulatory signals capable of effecting MRNA processing or gene expression. The polyadenylation signal is usually characterized by directing the addition of polyadenylic acid tracks to the 3' end of the mRNA precursor. Polyadenylation The sequence can also be derived from the promoter selected to express the gene, and can be specifically modified so as to increase translation of the mRNA.

To aid in identification of transformed plant cells, the vector of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the modified peptidyl transferase gene of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The vector constructs of the present invention can be introduced into plant cells using Ti plasmids, Ri plasmids, plant virus vectors, direct DNA transformation, microinjection, electroporation, etc. For reviews of such techniques see for example Weissbach and Weissbach, *Methods for Plant Molecular Biology*, Academy Press, New York VIII, pp. 421–463 (1988); and Geierson and Corey, *Plant Molecular Biology*, 2d Ed. (1988).

Suitable plant hosts include but are not limited to corn, barley, wheat, rice, rye, oats and millet.

Techniques for generating transgenic animals have been developed and optimized in mice (Hogan et al., 1986, Manipulation of the mouse embryo: a laboratory manual. Cold Spring Harbour Laboratory Press: New York), sheep (Wright et al., 1991, Bio-technology NY 9: 831–834), goats (Ebert and Schindler, 1993, Teriogenology, 39: 121–135) and pigs (Rexroad and Purcel, 1988, Proc. 11th Int. Congress of Animal Reproduction and Artificial Insem. 5: 29–35). In general such methods are based upon pronuclear micro injection of fertilized zygotes taken from superovulated female animals. Zygote pronuclei are micro injected with several hundred copies of the novel gene construct, and then transferred to recipient females for the remainder of the gestation period. Confirmation of transgene integration is by Southern hybridization of somatic tissues taken from the offspring, and analysis of gene product or gene function. Gene replacement experiments will permit the insertion of a modified peptidyl transferase in place of an animals endogenous wild-type (susceptible) gene which may confer the animal with a higher level of resistance to the effect of mycotoxin (Stacey et al., 1994, Mol. cell Biol. 14: 1009–1016).

Suitable animal hosts include any animal which has, at least as a part of its diet, the food grains referred to above as suitable plant hosts. These animals would include but are not limited to cows, sheep, goats, pigs, horses, poultry and even man. As noted previously, swine are very sensitive to the mycotoxins.

When specific sequences are referred to in the present invention, it is understood that these sequences include within their scope sequences that are "substantially homologous" to said specific sequences. Sequences are "substantially homologous" when at least about 70%, preferably at least about 80% and most preferably at least about 90 to 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389).

The specific sequences, referred to in the present invention, also include sequences which are "functionally equivalent" to said specific sequences. In the present invention functionally equivalent sequences refer to sequences which although not identical to the specific sequences provide the same or substantially the same function. DNA sequences that are functionally equivalent include any substitution, deletion or addition within the sequence. With reference to the present invention functionally equivalent sequences will provide resistance to the trichothecenes. As has been described before, the modified gene of the present invention must still retain peptidyl transferase activity but have reduced binding capabilities for the mycotoxin.

Thus, a further aspect of the invention is a transformed plant, transformed with the modified peptidyl transferase gene, wherein the transformed plant has increased resistance to Fusarium infestation.

In a further aspect of the invention there is provided a transformed animal, transformed with the modified peptidyl transferase gene, wherein the transformed animal is more tolerant to the trichothecene mycotoxins.

In yet another aspect of the present invention there is provided a method of conferring resistance to Fusarium infestation comprising the steps of: providing a modified gene, wherein the wild type form of said gene encodes a peptidyl transferase; and transforming a suitable plant with said modified gene.

In yet another aspect of the present invention there is provided a method of increasing tolerance in animals to trichothecene mycotoxins comprising the steps of: providing a modified gene, wherein the wild type form of said gene encodes a peptidyl transferase; and transforming a suitable animal with said modified gene.

Another aspect of the present invention is the use of the modified gene as a selectable marker in transformation experiments. Selectable marker genes such as the neomycin phosphotransferase npt II from bacterial transposons, or the hygromycin phosphotransferase hpt, or the mammalian dihydrofolate reductase gene dhfr have been successfully employed in many plant systems (Sproule et al., 1991, Theor. Appl. Genet, 82: 450–456; Dijak et al., 1991, Plant Cell Tissue and Organ Culture 25: 189–197). These genes have permitted the use of the antibiotics kanamycin, hygromycin and methotrexate respectively, in the selection of transgenic plants and at the protoplast level for the selection of somatic hybrids. Alternatively selection strategies have utility in science for the performance of multiple transformations, that is the repeated transformation of one plant with several different genes. To effect this, new and effective selective agents are desirable. Novel selection strategies based on genes which detoxify compounds other than antibiotics are also useful in cases where the use of antibiotics degrading or detoxification genes are not permitted or wanted in the transgenic organism. Under these cases it would be desirable to have a gene which confers a useful phenotype (disease resistance) as a selectable marker.

According to the present invention plant or animal cells that are exposed to DON are unable to proliferate in the presence of this toxin. Cell lines transformed with the modified gene of the present invention are more resistant to DON and will grow in a medium containing from 0.1 ppm to 50 ppm of DON. In one example of the present invention 0.5 to 10 ppm DON can be used in a selection medium. Thus the modified gene can be used as a selectable marker in transformation experiments, wherein only the cell lines that have become transformed with a vector containing the modified gene will grow in a selection medium containing DON. Thus, for example, the modified gene of the present invention could be used as a selectable marker in plant or animal transformation experiments in the same manner as genes providing resistance to gentamycin, hygromycin, kanamycin, and the like are presently used.

While this invention is described in detail with particular reference to preferred embodiments thereof, said embodiments are offered to illustrate but not limit the invention.

EXAMPLES

Example 1
Modification of the Rice Peptidyl Transferase Gene

The wildtype DNA sequence of the yeast Tcm1 gene was obtained from M. Bolotin-Fukuhara of the Yeast Genome Sequencing Project. Upon comparison of the Tcm1 DNA sequence with the mutant tcm1 sequence, a single base pair change was observed. This change converts a tryptophan (Tcm1) to a cysteine (tcm1) at residue 255 in the proposed RPL3 protein (FIG. 1).

In this example of the present invention, the corresponding rice Rpl3 gene was converted to a form resembling that of the yeast trichodermin resistance gene (tcml).

A rice Rpl3 cDNA, containing a 21 bp 5' non-coding region, a 1170 bp coding region, and a 177 bp 3' non-coding region (including a partial polyA tail), was kindly provided by Dr. A. Kato (Hokkaido University, Japan). The cDNA (originally named T82, renamed pOSRPL3) was received as a 1368 bp insert in the SmaI/lEcoRI site of pIBI31. This rice cDNA was randomly cloned from rice suspension culture cells (Uchimaya et al., 1992, Plant J. 2:1005–1009). A database search had revealed sequence homology with numerous ribosomal protein L3 genes (Nishi et al., 1993, Biochimica et Biophysica Acta 1216:110–112).

The proposed proteins coded for by the rice Rpl3 and the yeast Tcm1 genes share 65% amino acid identity. The tryptophan-to-cysteine change observed between the yeast gene alleles lies within a region well conserved in the rice gene; 17 amino acids 5', the tryptophan residue itself, and 3 amino acids 3' of the tryptophan are completely conserved between rice and yeast (FIG. 2 and Table 1).

Thus, site specific mutagenesis was employed to modify the rice Rpl3 cDNA to resemble the yeast tcml gene at the critical site.

pOSRPL3 was digested with XbaI and Nael, yielding a 1722 bp fragment encompassing the Rpl3 cDNA. This fragment was subcloned into the XbaI/HpaI site of the pALTER-EX1 vector (Promega) and named pALTRPL3. An 18 bp oligomer (5'-GGCTGGATGGCAGGCACC; SEQ ID No.: 4) was used to produce the desired mutation with the aid of the Altered Sites kit (Promega). DNA sequencing confirmed the mutagenesis was successful and the resultant clone was named pALTRPLC4.

Example 2

Vector Construction and Transformation

The upstream XbaI site and an EcoRI site 8 bp past the rice Rpl3 TAG stop codon were used to subclone either the unmodified or modified form of the gene into pCAMterX. pCAMterX is derived from pBIN19 (Bevan, M., 1984, Nucleic Acids Research, 12:8711–8721; FIG. 3) and has had a 70S CaMV promoter, multiple cloning site, and nos 3' terminator added. Plasmids containing the unmodified and modified Rpl3 genes subcloned into pCAMterX (FIG. 4) were named pCARPL3 and pCARPLC4, respectively. These two clones were transformed into Agrobacterium strain GV3101/pmp90 which was subsequently used to transform *Nicotiana tabacum* cultivar Delgold and *N. debneyi.* Transformed lines of *N. tabacum* and *N. debneyi* were selected on regeneration medium (Sproule et al. 1991, Theor. Appl. Genet. 82:450–456) containing 150 mg/L kanamycin.

Example 3

Plant Transformation

The vectors containing the unmodified and modified Rpl3 genes (pCARPL3 and pCARPLC4 respectively) were used to transform wild-type tobacco (*Nicotiana tobacum*) and a wild, diploid species N. debneyi. Both genes were transferred into these tobacco species at equal frequencies which suggests that neither rice gene had a negative effect on growth, regeneration, or seed production. For example, 70 and 63 independent transgenic lines of *N. debneyi* were recovered for the pCARPL3 and pCARPLC4 genes, respectively. Southern hybridization data and progeny testing of seeds from these transgenic plants was used to verify that the plants chosen for detailed analysis had single copy insertions.

Example 4

Protoplast Isolation and Culture

Seed harvested from transgenic *Nicotiana tabacum* and *N. debneyi* were surface sterilized in 70% Javex solution for 2–3 min followed by 5 rinses in sterile distilled water. They were planted (20 seeds per 60×20 mm petri plate) onto the surface of agar-solidified B5 medium (Gibco) containing 150 mg/L kanamycin and maintained at 25° C. in 16 hr daylength of 100 uE m sec. Those seedlings which germinated and remained green following two weeks of selection were transferred to fresh petri plates containing half strength MS medium (Gibco) lacking kanamycin. These plants were maintained inside sterile Magenta containers in a growth room at 25° C. in 16 hr daylength of 100 uE m sec.

The protoplast isolation from leaf mesophyll cells was as described by Sproule et al. (1991, Theor. Appl. Genet. 82:450–456). An enzyme solution of 1% (w/v) cellulase R-10 and macerozyme R-10 in 0.45M mannitol salt solution was filter sterilized and 20 mls was aliquoted to sterile 100×15 mm petri dishes. Five leaves of each donor plant were excised and floated abaxial side down over the enzyme solution. Petri dishes were sealed with parafilm, incubated in a humid box in a dark growth chamber at 28° C. for 17 hrs with gentle agitation. The liberated protoplasts were separated from tissue debris by filtration through a sterile 88 um mesh nylon funnel. The protoplast-enzyme solution was aliquoted into round-bottom sterile glass test tubes and centrifuged at 900 rpm for 10 min. Isolated protoplasts were separated from cellular debris by flotation on the surface of 4 mls of sterile 0.6M sucrose solution with an overlay of 0.5 mls of SCM (0.45M sorbitol, 10 mg/L CaC12.2H20, 5 mg/L MES morpholinoethane sulfonic acid; pH 5.8). Purified protoplasts were recovered from the SCM interface with sterile pipettes. Protoplasts were adjusted to a density of $5\times10^4$ cells/ mL with a haemocytometer, in liquid NT medium (Nagata and Takebe, 1991, Planta 99: 12–20) containing 0.4M glucose as osmoticum.

A stock solution of DON, produced according to the method of Greenhalgh et al. (1986, J. Agric. Food Chem. 34: 98–102) was used to adjust the concentration of DON toxin in some protoplast cultures to either 0, 0.1, 1.0, 5.0, or 10.0 ppm. All protoplast cultures were 2 mLs of liquid, incubated in sterile 60×15 mm petri dishes at 28° C. in darkness. After one week of culture, the osmotic concentration of the medium was adjusted by the addition of 0.5 mLs of NT medium containing 0.3M glucose, and the protoplast cultures were moved to low light (10 uE m sec) at 25° C.

The wild-type plants were shown to be susceptible to DON at 0.5 to 10 ppm in culture medium. The effect of DON on these protoplasts was to reduce the ability of protoplasts to reform cell walls, reduce the division frequency (mitotic index of the cells), and reduce the plating efficiency (number of micro colonies formed) of protoplasts relative to those cultured in the absence of DON.

The viability of protoplasts of the genotype Rpl3:c258 (C4 lines) were not significantly affected by culture for 20 days in medium supplemented with 0.5 to 25 ppm DON. Whereas the viability of protoplasts containing Rpl3.c258 in the absence of DON was about 65%, it was 56% when these protoplasts were cultured in the presence of 25 ppm DON. Protoplasts from wild-type tobacco plants when cultured in NT medium supplemented with 25 ppm DON had viability of 18% while those from transgenic plants with the rice Rpl3 gene (C3 lines) had less than 10% viability. This effect on leaf mesophyll protoplasts was not due to the general effect of each genotype, since in the absence of DON each line had viabilities in NT medium ranging from 58% to 66%. The pronounced differences between genotypes became apparent when protoplasts were cultured in the presence of the mycotoxin DON.

Protoplasts were also cultured over 2 mLs agarose underlayers (0.4% w/v) inside sterile 60×15 mm petri dishes. The agarose underlayers contained either 0, 0. 1, 1.0, 10, or 25 ppm DON. Protoplasts in these cultures were suspended in liquid NT medium at a density of $1\times10^5$ per mL and cultured as in Sproule et al. (1991, Theor. Appl. Genet. 82:450–456).

When protoplasts were cultured on medium supplemented with DON, noticeable differences were observed in micro colony formation (cell colonies from isolated protoplasts). Colonies from protoplasts containing Rpl 3 did not often develop into calli, and therefore were not transferred to regeneration medium whereas micro colonies containing Rpl 3:c258 were capable of transfer to regeneration medium.

Example 5

Cell Suspension Cultures

Cell suspension cultures from primary transgenic or wild type tobacco plants were initiated from leaf callus cultures. Two grams of callus was ground in a sterile blender, and the homogenized tissue was used to inoculate 33 mLs of liquid MS medium containing 2 mg/L 2,4-D in a sterile 33 InL Erlenmeyer flask. Cell suspensions were maintained on an orbital shaker at 150 rpm under a 16 hr daylength at 25° C. with weekly sub-culture of 5–10 mls of cells into 33 mLs of fresh medium.

Growth measurements of cell suspensions were taken after the cultures had equilibrated in growth conditions for 12 weeks. The measure of weight gain was determined by plating 1 mL of cell suspension on sterile Whatman filter paper placed on the surface of 10 mLs of agar-solidified MS medium containing either 0 or 25 ppm DON. At 4 day intervals, the fresh weight of each filter paper was determined under aseptic conditions and then the cells were re-cultured on the same medium. Cells of both genotypes were equally capable of growth when transferred to agar-solidified medium supplemented with kanamycin, indicating the stability and presence of the transgenes in these cultures.

The increase in cell volume was measured by inoculating 5 mLs of cells into 35 mLs of liquid MS medium supplemented with either 0 or 25 ppm DON. At 3 day intervals, the entire contents of each flask was transferred to sterile conical calibrated tubes, and the packed cell volume was recored (Table 2). The cell were returned to culture in the same medium.

TABLE 2

Average Volume Increase of Transgenic Tobacco Cells Grown in the Presence or Absence of DON Mycotoxin for 12 Days

| Cell Line | Concentration of DON (ppm) | Average % Vol. Increase |
|---|---|---|
| C4 | 0 | 45 |
| C3 | 0 | 40 |
| C4 | 25 | 41 |
| C3 | 25 | 13 |

DON at 25 ppm was sufficient to inhibit the packed cell volume, and the fresh weight gain of cell suspensions of pCARPL3 plants. These levels of DON had a less serious impact on packed cell volume, or cell fresh weight gain of cultures of pCARPLC4 plants (Table 3 and FIG. 5*a* and FIG. 5*b*).

TABLE 3

Average Growth Rate of Transgenic Tobacco Cells Grown in the Presence or Absence of DON Mycotoxin for 16 Days

| Cell Line | Concentration of DON (ppm) | Average % Wt. Increase |
|---|---|---|
| C4 | 0 | 22.5 |
| C3 | 0 | 24.5 |
| C4 | 25 | 21.5 |
| C3 | 25 | 8.5 |

DON was also capable of inhibiting the formation of callus on leaf explants cultured in vitro from leaves of wild-type and pCAPRL3 plants, whereas explants from pCARPLC4 plants were capable of regeneration in the presence of DON.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiment of the invention in which an exclusive property of privilege is claimed are defined as follows:

1. A modified nucleic acid, wherein the wild type form of said nucleic acid encodes a ribosome L3 protein and wherein a host transformed with said modified nucleic acid is resistant to trichothecene mycotoxins, wherein the modification is sufficient to reduce the mycotoxin binding capabilities of the encoded ribosome L3 protein but is insufficient to destroy the function of the nucleic acid as a ribosomal protein gene and wherein the modification is a single amino acid substitution for Trp at position 255 (based on the yeast numbering), with the proviso that said nucleic acid is not from *Saccharomyces cerevisiae*.

2. The modified nucleic acid of claim 1, wherein the source of the nucleic acid encoding the ribosomal L3 protein is selected from the group consisting of: rice, *Arabidopsis thalicina,* rat, mice, human, and *C. elegans*.

3. The modified nucleic acid of claim 2, wherein the nucleic acid encoding the ribosomal L3 protein nucleic acid is a rice gene.

4. The modified nucleic acid of claimed 3, wherein the nucleic acid has a sequence which will encode the amino acid sequence shown in SEQ ID No.:3, with the sequence encoding a cysteine at position 258 or a functional equivalent thereof.

5. A cloning vector containing a modified ribosomal L3 protein nucleic acid as defined in claim 1.

6. The cloning vector of claim 5, wherein the nucleic acid encoding the ribosomal L3 protein is selected from the group consisting of: rice, *Arabidopsis thaliana,* rat, mice, human, and *C. elegans*.

7. The cloning vector of claim 6, wherein the nucleic acid encoding the ribosomal L3 protein is a rice gene.

8. The cloning vector of claim 7, wherein the nucleic acid has a sequence which will encode the amino acid sequence shown in SEQ ID No.:3, with the sequence encoding a cysteine at position 258 or a functional equivalent thereof.

9. A transformed plant transformed with a modified ribosomal L3 protein nucleic acid of claim 1, wherein said transformed plant is resistant to Fusarium infestation.

10. The plant of claim 9, wherein the nucleic acid encoding the ribosomal L3 protein is selected from the group consisting of: rice *Arahidopsis thaliana,* rat, mice, human, and *C. elegans*.

11. The plant of claim 10, wherein the nucleic acid encoding the ribosomal L3 protein is a rice gene.

12. The plant of claim 11, wherein the nucleic acid has a sequence which will encode the amino acid sequence shown in SEQ ID No.:3, with the sequence encoding a cysteine at position 258 or a functional equivalent thereof.

13. Seeds from a transformed plant as defined in claim 9, wherein said seeds retain said nucleic acid.

14. A method of increasing resistance to Fusarium infestation by transforming a suitable plant with a modified nucleic acid as defined in claim 1, wherein the plant transformed with said nucleic acid has increased resistance is resistant to trichothecene mycotoxins and wherein said method comprises the steps of providing a modified nucleic acid and transforming a suitable plant with said nucleic acid.

15. A method of using the modified nucleic acid as defined in claim 1, as a selectable marker in transformation experiments of plants comprising the steps of:

cotransforming a modified Rpl3 nucleic acid into a plant to produce a transgenic plant; and selecting for said transgenic plant on a media supplemented with a trichothecene mycotoxin.

16. Seeds from a transformed plant as defined in claim 10, wherein said seeds retain said nucleic acid.

17. Seeds from a transformed plant as defined in claim 11, wherein said seeds retain said nucleic acid.

18. Seeds from a transformed plant as defined in claim 12, wherein said seeds retain said nucleic acid.

* * * * *

SEQUENCE LISTING

```
(1) GENERAL INFORMATION:

(iii) NUMBER OF SEQUENCES: 4

(2) INFORMATION FOR SEQ ID NO: 1:

(i) SEQUENCE CHARACTERISTICS:
          (A) LENGTH: 350 amino acids
```

(B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
                20                  25                  30

Pro Lys Asp Asp Arg Ser Lys Pro Val Ala Leu Thr Ser Phe Leu Gly
            35                  40                  45

Tyr Lys Ala Gly Met Thr Thr Ile Val Arg Asp Leu Asp Arg Pro Gly
        50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
                100                 105                 110

Glu Val Lys Arg Arg Phe Tyr Lys Asn Trp Tyr Lys Ser Lys Lys Lys
                115                 120                 125

Ala Phe Thr Lys Tyr Ser Ala Lys Tyr Ala Gln Asp Gly Ala Gly Ile
            130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
                180                 185                 190

Asp Trp Ala Arg Glu His Phe Glu Lys Thr Val Ala Val Asp Ser Val
                195                 200                 205

Phe Glu Gln Asn Glu Met Ile Asp Ala Ile Ala Val Thr Lys Gly His
                210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Trp His
                245                 250                 255

Pro Ala His Val Met Trp Ser Val Ala Arg Ala Gly Gln Arg Gly Tyr
                260                 265                 270

His Ser Arg Thr Ser Ile Asn His Lys Ile Tyr Arg Val Gly Lys Gly
                275                 280                 285

Asp Asp Glu Ala Asn Gly Ala Thr Ser Phe Asp Arg Thr Lys Lys Thr
            290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala
                340                 345                 350

(2) INFORMATION FOR SEQ ID NO: 2:

(i) SEQUENCE CHARACTERISTICS:
        (A) LENGTH: 350 amino acids

-continued

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Ser His Arg Lys Tyr Glu Ala Pro Arg His Gly His Leu Gly Phe
1               5                   10                  15

Leu Pro Arg Lys Arg Ala Ala Ser Ile Arg Ala Arg Val Lys Ala Phe
                20                  25                  30

Pro Lys Asp Asp Arg Ser Lys Pro Val Ala Leu Thr Ser Phe Leu Gly
            35                  40                  45

Tyr Lys Ala Gly Met Thr Thr Ile Val Arg Asp Leu Asp Arg Pro Gly
        50                  55                  60

Ser Lys Phe His Lys Arg Glu Val Val Glu Ala Val Thr Val Val Asp
65                  70                  75                  80

Thr Pro Pro Val Val Val Gly Val Val Gly Tyr Val Glu Thr Pro
                85                  90                  95

Arg Gly Leu Arg Ser Leu Thr Thr Val Trp Ala Glu His Leu Ser Asp
                100                 105                 110

Glu Val Lys Arg Arg Phe Tyr Lys Asn Trp Tyr Lys Ser Lys Lys Lys
                115                 120                 125

Ala Phe Thr Lys Tyr Ser Ala Lys Tyr Ala Gln Asp Gly Ala Gly Ile
            130                 135                 140

Glu Arg Glu Leu Ala Arg Ile Lys Lys Tyr Ala Ser Val Val Arg Val
145                 150                 155                 160

Leu Val His Thr Gln Ile Arg Lys Thr Pro Leu Ala Gln Lys Lys Ala
                165                 170                 175

His Leu Ala Glu Ile Gln Leu Asn Gly Gly Ser Ile Ser Glu Lys Val
                180                 185                 190

Asp Trp Ala Arg Glu His Phe Glu Lys Thr Val Ala Val Asp Ser Val
                195                 200                 205

Phe Glu Gln Asn Glu Met Ile Asp Ala Ile Ala Val Thr Lys Gly His
                210                 215                 220

Gly Phe Glu Gly Val Thr His Arg Trp Gly Thr Lys Lys Leu Pro Arg
225                 230                 235                 240

Lys Thr His Arg Gly Leu Arg Lys Val Ala Cys Ile Gly Ala Cys His
                245                 250                 255

Pro Ala His Val Met Trp Ser Val Ala Arg Ala Gly Gln Arg Gly Tyr
                260                 265                 270

His Ser Arg Thr Ser Ile Asn His Lys Ile Tyr Arg Val Gly Lys Gly
                275                 280                 285

Asp Asp Glu Ala Asn Gly Ala Thr Ser Phe Asp Arg Thr Lys Lys Thr
            290                 295                 300

Ile Thr Pro Met Gly Gly Phe Val His Tyr Gly Glu Ile Lys Asn Asp
305                 310                 315                 320

Phe Ile Met Val Lys Gly Cys Ile Pro Gly Asn Arg Lys Arg Ile Val
                325                 330                 335

Thr Leu Arg Lys Ser Leu Tyr Thr Asn Thr Ser Arg Lys Ala
                340                 345                 350

(2) INFORMATION FOR SEQ ID NO: 3:

(i) SEQUENCE CHARACTERISTICS:
        (A) LENGTH: 389 amino acids
```

(B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Met Ser His Arg Lys Phe Glu His Pro Arg His Gly Ser Leu Gly Phe
1               5                   10                  15

Leu Pro Arg Lys Arg Ser Ser Arg His Arg Gly Lys Val Lys Ser Phe
            20                  25                  30

Pro Lys Asp Asp Val Ser Lys Pro Cys His Leu Thr Ser Phe Val Gly
            35                  40                  45

Tyr Lys Ala Gly Met Thr His Ile Val Arg Glu Val Glu Lys Pro Gly
50                      55                  60

Ser Lys Leu His Lys Lys Glu Thr Cys Glu Ala Val Thr Ile Ile Glu
65                  70                  75                  80

Thr Pro Pro Leu Val Ile Val Gly Leu Val Ala Tyr Val Lys Thr Pro
                85                  90                  95

Arg Gly Leu Arg Ser Leu Asn Ser Val Trp Ala Gln His Leu Ser Glu
            100                 105                 110

Glu Val Arg Arg Arg Phe Tyr Lys Asn Trp Cys Lys Ser Lys Lys Lys
            115                 120                 125

Ala Phe Thr Lys Tyr Ala Leu Lys Tyr Asp Ser Asp Ala Gly Lys Lys
            130                 135                 140

Glu Ile Gln Met Gln Leu Glu Lys Met Lys Lys Tyr Ala Ser Ile Val
145                 150                 155                 160

Arg Val Ile Ala His Thr Gln Ile Arg Lys Met Lys Gly Leu Lys Gln
                165                 170                 175

Lys Lys Ala His Leu Met Glu Ile Gln Ile Asn Gly Gly Thr Ile Ala
            180                 185                 190

Asp Lys Val Asp Tyr Gly Tyr Lys Phe Phe Glu Lys Glu Ile Pro Val
            195                 200                 205

Asp Ala Val Phe Gln Lys Asp Glu Met Ile Asp Ile Ile Gly Val Thr
            210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                245                 250                 255

Ala Trp His Pro Ala Arg Val Ser Tyr Thr Val Ala Arg Ala Gly Gln
            260                 265                 270

Asn Gly Tyr His His Arg Thr Glu Met Asn Lys Lys Val Tyr Lys Ile
            275                 280                 285

Gly Lys Ser Gly Gln Glu Ser His Ala Ala Cys Thr Glu Phe Asp Arg
290                 295                 300

Thr Glu Lys Asp Ile Thr Pro Met Gly Gly Phe Pro His Tyr Gly Val
305                 310                 315                 320

Val Lys Gly Asp Tyr Leu Met Ile Lys Gly Cys Cys Val Gly Pro Lys
                325                 330                 335

Lys Arg Val Val Thr Leu Arg Gln Ser Leu Leu Lys Gln Thr Ser Arg
            340                 345                 350

Leu Ala Leu Glu Glu Ile Lys Leu Lys Phe Ile Asp Thr Ser Ser Lys
            355                 360                 365

Phe Gly His Gly Arg Phe Gln Thr Thr Asp Glu Lys Gln Arg Phe Phe
            370                 375                 380

-continued

```
Gly Lys Leu Lys Ala
385

(2) INFORMATION FOR SEQ ID NO: 4:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION:   /desc = "oligomer"

(xi) SEQUENCE DESCRIPTION: SEQ ID NO: 4:

GGCTGGATGG CAGGCACC                                                       18
```